United States Patent [19]

Brown et al.

[11] 4,041,175

[45] Aug. 9, 1977

[54] USE OF PLEUROMUTILIN FOR THE TREATMENT OF SWINE DYSENTERY

[75] Inventors: William E. Brown, Princeton; Charles O. Baughn, Flemington, both of N.J.; Wayne H. Linkenheimer, Washington Crossing, Pa.

[73] Assignee: E. R. Squibb & Sons, Inc., Princeton, N.J.

[21] Appl. No.: 469,260

[22] Filed: May 13, 1974

[51] Int. Cl.² ............................................. A61K 31/22
[52] U.S. Cl. .................................................... 424/311
[58] Field of Search ................................ 424/305, 311

[56] References Cited

FOREIGN PATENT DOCUMENTS 1,111,010  4/1968  United Kingdom

OTHER PUBLICATIONS

*The Merck Veterinary Manual*, 3rd. Ed., pp. 461-463, Merck & Co., Rahway, N.J., USA (1967).

*Primary Examiner*—Frederick E. Waddell
*Attorney, Agent, or Firm*—Lawrence S. Levinson; Merle J. Smith; Donald J. Barrack

[57] ABSTRACT

Swine dysentery can be treated by the oral administration to swine suffering from the disease of an effective amount of pleuromutilin.

4 Claims, No Drawings

USE OF PLEUROMUTILIN FOR THE TREATMENT OF SWINE DYSENTERY

BACKGROUND OF THE INVENTION

Swine dysentery is a mucohemorrhagic, diarrheal disease that affects primarily weanling pigs, but may affect larger pigs. The disease is often referred to as bloody scours, bloody dysentery, hemorrhagic dysentery, mucohemorrahagic diarrhea, or vibrionic dysentery. The disease occurs in many swine-raising areas of the world.

Morbidity is usually greater than 90% in weanling pigs and mortality may reach 75%. Experimentally, swine dysentery may decrease the rate of weight gain two fold and decrease efficiency of feed conversion threefold, as compared with uninfected control pigs. The disease causes tremendous financial losses because of death and decreased rate of growth of infected swine.

The cause of swine dysentery is, as yet, ill defined. In the past, Vibrio coli has been associated with the disease. More recently, a large spirochete Treponema hyodysenteriae, acting in association with other intestinal microorganisms, is thought to be the cause of the disease. At present, the only reliable method of experimental reproduction of the disease is to inoculate susceptible pigs with colonic mucosa and colonic contents of pigs acutely affected with the disease.

The outlook for successful prevention and control of swine dysentery has not been promising because no product previously approved for use in the United States has completely prevented recurrence of the disease. Many swine owners have ultimately had to depopulate, clean, disinfect, and restock when the disease became enzootic. It appears that any immunity that develops from natural infection is short lived, and little optimism is expressed concerning the early development of a useful immunologic agent or vaccine.

SUMMARY OF THE INVENTION

It is an object of this invention to provide an effective method of treating swine dysentery.

It is a further object of this invention to treat swine dysentery by the oral administration of an agent that can be added to the swine's feed or the swine's drinking water.

These and other objects, that will be readily apparent to a person of ordinary skill in the art, are realized by the method of this invention. The method of this invention comprises orally administering to swine infected with swine dysentery an effective amount of pleuromutilin.

DETAILED DESCRIPTION OF THE INVENTION

Swine can be effectively treated for swine dysentery by the oral administration of pleuromutilin. For the treatment of swine dysentery, pleuromutilin can be administered to a swine in an amount of from about 0.5 milligrams/kilograms of animal body weight/day to 20 milligrams/kilogram of animal body weight/day, preferably about 3 milligrams/kilograms of animal body weight/day to 15 milligrams/kilogram of animal body weight/day.

Pleuromutilin is a diterpene antibiotic first isolated in 1951 by Kavanagh et al from culture broths of Pleurotus multilus; see, for example, Kavanagh et al, Proc. Nat. Acad. Sci., 37, 570 (1951). More recently, pleuromutilin has been isolated from cultures of Clitopilus passeckerianus; see British Pat. No. 1,111,010. The structure of pleuromutilin has been elucidated by Birch et al to be as follows:

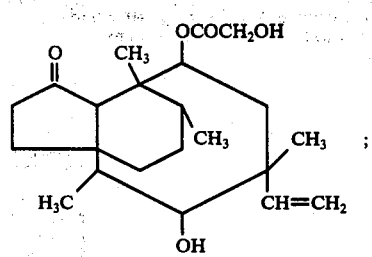

see Birch et al, Chemistry and Industry (London) 1963, 374.

British Pat. No. 1,111,010, in addition to disclosing a process for the isolation of pleuromutilin, discloses that pleuromutilin can be administered to farm animals such as pigs, to achieve an optimum rate of weight gain and an improved utilizaton of feed. Netherlands Pat. No. 69/11082 discloses generally that pleuromutilin can be used in veterinary medicine against animal-pathogenic germs.

Pleuromutilin for the treatment of swine dysentery can be administered orally to a swine infected with the disease in the form of a tablet, capsule, powder, or the like. It is preferred, however, that pleuromutilin be administered in the feed of the swine.

The following example demonstrates the effectiveness of pleuromutilin in treating swine dysentery.

EXAMPLE

Fourteen male and female pigs, 6 to 8 weeks of age are weighed and 10 of the pigs infected orally with the colonic scrapings from a pig which has been acutely infected with swine dysentery. Darkfield microscopic examination of the infecting material shows numerous spirochetes (T. hyodysenteriae).

Immediately following infection, 5 of the infected pigs are randomly assigned to a pen and receive swine starter ration with pleuromutilin added at the rate of 100 gram/ton of ration (0.011%). Treatment begins immediately following infection. The remaining 5 infected pigs received swine starter ration which is non-medicated. The 4 non-infected pigs serve as age and condition controls and also receive non-medicated swine starter ration.

The swine starter ration used in this experiment consists of the following:

| Ingredients | Pounds |
| --- | --- |
| Corn meal | 1311 |
| Wheat midds | 100 |
| Soybean | 405 |
| Menhaden meal | 40 |
| Dried whey | 50 |
| Calcium phosphate | 30 |
| Salt | 10 |
| Mineral mix[1] | 2 |
| Molasses | 50 |
| Vitamin mix[2] | 2 |
| | 2000 |

1. The swine mineral mix at 2 pounds per ton of starter ration adds the following trace minerals:
    Copper            5.4 grams

| | |
|---|---|
| Iron | 68.0 grams |
| Manganese | 18.2 grams |
| Zinc | 45.4 grams |
| Iodine | .2 grams |

2. The swine vitamin mix at 2 pounds per ton of starter ration adds the following vitamins:

| | |
|---|---|
| Vitamin A | 3000 IU |
| Vitamin D | 1000 IU |
| Vitamin E | 20 IU |
| Vitamin $B_{12}$ | 20 μg |
| Riboflavin | 3 mg |
| Pantothenic acid | 10 mg |
| Niacin | 20 mg |
| Choline | 200 mg |

Treatment continues for 5 days at which time all pigs are again weighed and rectal swabs obtained from all pigs to determine the presence of *T. hyodysenteriae*.

The results are summarized in Table I below. The data show that the infected non-treated controls gained a means of 0.89 kilograms during the five day period while the non-infected controls gained a mean of 2.90 kilograms. The pigs treated with pleuromutilin had a mean gain of 2.21 kilograms which did not differ significantly from the mean gain of the non-infected pigs.

At the end of the test 4 out of 5 of the infected, non-treated pigs still harbored *T. hyodysenteriae* while the organism had been eliminated from all of the treated pigs.

Table I

| | | Mean Body Weight | | | |
|---|---|---|---|---|---|
| Treatment | % in diet | at infection | 5 days post-infection | Mean gain | Presence of treponema/total tested* |
| | | kg | kg | kg | |
| No infection, no treatment | none | 6.54 | 9.44 | 2.90 | 0/4 |
| Infected, pleuromutilin treatment | 0.011 | 6.58 | 8.79 | 2.21 | 0/5 |
| Infected, no treatment | none | 6.64 | 7.53 | 0.89 | 4/5 |

*Presence of treponema determined by microscopic examination of simple smears prepared from rectal swabs taken at the termination of the test.

What is claimed is:

1. A method for treating swine dysentery which comprises orally administering to an infected swine an effective amount of pleuromutilin.

2. A method in accordance with claim 1 wherein the pleuromutilin is administered in an amount of from 0.5 milligrams per kilogram of animal body weight per day to 20 milligrams per kilogram of animal body weight per day.

3. A method in accordance with claim 1 wherein the pleuromutilin is administered in an amount of from 3 milligrams per kilogram of animal body weight per day to 15 milligrams per kilogram of animal body weight per day.

4. A method in accordance with claim 1 which comprises first combining pleuromutilin with the swine's feed.

* * * * *